US012788766B2

(12) United States Patent
Guy et al.

(10) Patent No.: US 12,788,766 B2
(45) Date of Patent: Nov. 10, 2026

(54) CANNABIDIOL-TYPE CANNABINOID COMPOUND

(71) Applicant: Jazz Pharmaceuticals Research UK Limited, Sittingbourne (GB)

(72) Inventors: Geoffrey Guy, Sittingbourne (GB); Volker Knappertz, Sittingbourne (GB); Benjamin Whalley, Sittingbourne (GB); Royston Gray, Sittingbourne (GB); Jacqueline Cilia, Sittingbourne (GB); Amesha Patel, Sittingbourne (GB); Hannah Straker, Sittingbourne (GB)

(73) Assignee: JAZZ PHARMACEUTICALS RESEARCH UK LIMITED, Sittingbourne (GB)

( * ) Notice: Subject to any disclaimer, the term of this patent is extended or adjusted under 35 U.S.C. 154(b) by 1183 days.

(21) Appl. No.: 17/296,066

(22) PCT Filed: Nov. 20, 2019

(86) PCT No.: PCT/GB2019/053284
§ 371 (c)(1),
(2) Date: May 21, 2021

(87) PCT Pub. No.: WO2020/104796
PCT Pub. Date: May 28, 2020

(65) Prior Publication Data

US 2022/0016048 A1 Jan. 20, 2022

(30) Foreign Application Priority Data

Nov. 21, 2018 (GB) ..................................... 1818935

(51) Int. Cl.
*A61K 31/00* (2006.01)
*A61K 36/185* (2006.01)
*A61P 25/08* (2006.01)

(52) U.S. Cl.
CPC ........ *A61K 31/658* (2023.05); *A61K 36/3482* (2024.05); *A61P 25/08* (2018.01)

(58) Field of Classification Search
None
See application file for complete search history.

(56) References Cited

U.S. PATENT DOCUMENTS 8,632,825 B2 1/2014 Velasco Diez et al.
8,790,719 B2 7/2014 Parolaro et al.
9,017,737 B2 4/2015 Kikuchi et al.
9,125,859 B2 9/2015 Whalley et al.
9,474,726 B2 10/2016 Guy et al.
9,675,654 B2 6/2017 Parolaro et al.
9,949,936 B2 4/2018 Guy et al.
9,949,937 B2 4/2018 Guy et al.
9,956,183 B2 5/2018 Guy et al.
9,956,184 B2 5/2018 Guy et al.
9,956,185 B2 5/2018 Guy et al.
9,956,186 B2 5/2018 Guy et al.
9,962,341 B2 5/2018 Stott et al.
10,039,724 B2 8/2018 Stott et al.
10,092,525 B2 10/2018 Guy et al.
10,098,867 B2 10/2018 Javid et al.
10,111,840 B2 10/2018 Guy et al.
10,137,095 B2 11/2018 Guy et al.
10,220,005 B2 3/2019 Martinez-Orgado et al.
10,226,433 B2 3/2019 Di Marzo et al.
10,583,096 B2 3/2020 Guy et al.
10,603,288 B2 3/2020 Guy et al.
10,653,641 B2 5/2020 Robson et al.
10,709,671 B2 7/2020 Guy et al.
10,709,673 B2 7/2020 Guy
10,709,674 B2 7/2020 Guy et al.
10,729,665 B2 8/2020 Whalley et al.
10,758,514 B2 9/2020 Liu et al.
10,765,643 B2 9/2020 Guy et al.
10,799,467 B2 10/2020 Whalley et al.
10,807,777 B2 10/2020 Whittle
10,849,860 B2 12/2020 Guy et al.
10,918,608 B2 2/2021 Guy et al.
10,966,939 B2 4/2021 Guy et al.
11,000,486 B2 5/2021 Wright et al.
11,065,209 B2 7/2021 Guy et al.
11,065,227 B2 7/2021 Stott et al.
11,096,905 B2 8/2021 Guy et al.
11,147,776 B2 10/2021 Stott et al.
(Continued)

FOREIGN PATENT DOCUMENTS

GB 2531093 A 4/2016
GB 2531282 A 4/2016
(Continued)

OTHER PUBLICATIONS

U.S. Appl. No. 14/741,829, filed Jun. 17, 2015.
U.S. Appl. No. 15/519,244, filed Apr. 14, 2017.
U.S. Appl. No. 15/640,033, filed Jun. 30, 2017.
U.S. Appl. No. 15/751,563, filed Feb. 9, 2018.
(Continued)

*Primary Examiner* — Michael V Meller
(74) *Attorney, Agent, or Firm* — COOLEY LLP

(57) ABSTRACT

The present invention relates to a cannabidiol (CBD) type cannabinoid compound for use as a medicament. The CBD-type cannabinoid, cannabidiol-C4 (CBD-C4), is a naturally occurring cannabinoid that can be found in minor quantities in the *cannabis* plant. Furthermore, the cannabinoid can be produced by synthetic means. Disclosed herein are data which demonstrate the efficacy of CBD-C4 in models of disease. In addition, a method for the production of CBD-C4 is described.

7 Claims, 4 Drawing Sheets

(56) References Cited

U.S. PATENT DOCUMENTS 11,147,783 B2 10/2021 Stott et al.
11,154,516 B2 10/2021 Guy et al.
11,154,517 B2 10/2021 Guy et al.
11,160,757 B1 11/2021 Wilkhu et al.
11,160,795 B2 11/2021 Guy et al.
11,207,292 B2 12/2021 Guy et al.
11,229,612 B2 1/2022 Wright et al.
11,291,631 B2 4/2022 Shah
11,311,498 B2 4/2022 Guy et al.
11,318,109 B2 5/2022 Whalley et al.
11,357,741 B2 6/2022 Guy et al.
11,400,055 B2 8/2022 Guy et al.
11,406,623 B2 8/2022 Guy et al.
11,413,266 B2 8/2022 Biróet al.
11,419,829 B2 8/2022 Whalley et al.
11,426,362 B2 8/2022 Wright et al.
11,446,258 B2 9/2022 Guy et al.
11,590,087 B2 2/2023 Guy et al.
11,633,369 B2 4/2023 Guy et al.
11,679,087 B2 6/2023 Guy et al.
11,684,598 B2 6/2023 Stott et al.
11,701,330 B2 7/2023 Guy et al.
11,766,411 B2 9/2023 Guy et al.
11,793,770 B2 10/2023 Stott et al.
11,806,319 B2 11/2023 Wilkhu et al.
11,865,102 B2 1/2024 Guy et al.
11,963,937 B2 4/2024 Guy
12,023,305 B2 7/2024 Whalley et al.
12,064,398 B2 8/2024 Wright et al.
12,064,399 B2 8/2024 Guy et al.
2015/0359756 A1 12/2015 Guy et al.
2017/0239193 A1 8/2017 Guy et al.
2017/0349517 A1 12/2017 Dickman et al.
2018/0071210 A1 3/2018 Wilkhu et al.
2018/0228751 A1 8/2018 Stott et al.
2018/0282250 A1 10/2018 Rutz et al.
2019/0167583 A1 6/2019 Shah
2019/0314296 A1 10/2019 Wright et al.
2019/0321307 A1 10/2019 Guy et al.
2019/0365667 A1 12/2019 Wright et al.
2020/0138738 A1 5/2020 Guy et al.
2020/0179303 A1 6/2020 Guy et al.
2020/0206152 A1 7/2020 Stott et al.
2020/0206153 A1 7/2020 Whalley et al.
2020/0237683 A1 7/2020 Whalley et al.
2020/0297656 A1 9/2020 Guy et al.
2020/0352878 A1 11/2020 Guy et al.
2021/0015789 A1 1/2021 Guy et al.
2021/0052512 A1 2/2021 Guy et al.
2021/0059949 A1 3/2021 Wilkhu et al.
2021/0059960 A1 3/2021 Wilkhu et al.
2021/0059976 A1 3/2021 Wilkhu et al.
2021/0069333 A1 3/2021 Velasco Diez et al.
2021/0093581 A1 4/2021 Guy et al.
2021/0169824 A1 6/2021 Guy et al.
2021/0177773 A1 6/2021 Guy et al.
2021/0244685 A1 8/2021 Guy et al.
2021/0267950 A1 9/2021 Guy et al.
2021/0290565 A1 9/2021 Guy et al.
2021/0330636 A1 10/2021 Guy et al.
2021/0401771 A1 12/2021 Guy et al.
2022/0000800 A1 1/2022 Guy et al.
2022/0008355 A1 1/2022 Guy et al.
2022/0023232 A1 1/2022 Guy et al.
2022/0040155 A1 2/2022 Guy et al.
2022/0062197 A1 3/2022 Stott et al.
2022/0087951 A1 3/2022 Knappertz
2022/0096397 A1 3/2022 Wright et al.
2022/0168266 A1 6/2022 Guy et al.
2022/0183997 A1 6/2022 Guy et al.
2022/0184000 A1 6/2022 Guy et al.
2022/0202738 A1 6/2022 Guy et al.
2022/0211629 A1 7/2022 Wilkhu et al.
2022/0226257 A1 7/2022 Guy et al.
2022/0233495 A1 7/2022 Silcock et al.
2022/0249396 A1 8/2022 Guy et al.
2022/0257529 A1 8/2022 Guy et al.
2022/0265573 A1 8/2022 Guy et al.
2022/0288055 A1 9/2022 Silcock et al.
2022/0362149 A1 11/2022 Shah
2022/0378714 A1 12/2022 Guy et al.
2022/0378715 A1 12/2022 Guy et al.
2022/0378738 A1 12/2022 Guy et al.
2022/0387347 A1 12/2022 Whalley et al.
2022/0395470 A1 12/2022 Whalley et al.
2022/0395471 A1 12/2022 Guy et al.
2023/0000789 A1 1/2023 Guy et al.
2023/0022487 A1 1/2023 Guy et al.
2023/0024312 A1 1/2023 Whalley et al.
2023/0026079 A1 1/2023 Guy et al.
2023/0032502 A1 2/2023 Guy et al.
2023/0038423 A1 2/2023 Silcock et al.
2023/0068885 A1 3/2023 Guy et al.
2023/0143812 A1 5/2023 Knappertz et al.
2023/0235825 A1 7/2023 Thompson et al.
2023/0248664 A1 8/2023 Guy
2023/0263744 A1 8/2023 Guy
2023/0277560 A1 9/2023 Checketts et al.
2023/0277561 A1 9/2023 Checketts et al.
2023/0277562 A1 9/2023 Checketts et al.
2023/0277563 A1 9/2023 Checketts et al.
2023/0285419 A1 9/2023 Checketts et al.
2023/0285420 A1 9/2023 Checketts et al.
2023/0285421 A1 9/2023 Checketts et al.
2023/0285422 A1 9/2023 Checketts et al.
2023/0285423 A1 9/2023 Checketts et al.
2023/0285424 A1 9/2023 Checketts et al.
2023/0285425 A1 9/2023 Checketts et al.
2023/0285426 A1 9/2023 Checketts et al.
2023/0285427 A1 9/2023 Checketts et al.
2023/0285428 A1 9/2023 Checketts et al.
2023/0301934 A1 9/2023 Whalley et al.
2023/0301936 A1 9/2023 Guy et al.
2023/0310464 A1 10/2023 Checketts et al.
2023/0372367 A1 11/2023 Checketts et al.
2023/0372368 A1 11/2023 Checketts et al.
2024/0016819 A1 1/2024 Craig
2024/0025858 A1 1/2024 Silcock et al.
2024/0033229 A1 2/2024 Guy et al.
2024/0033272 A1 2/2024 Checketts et al.
2024/0043388 A1 2/2024 Silcock et al.
2024/0050452 A1 2/2024 Craig et al.
2024/0091241 A1 3/2024 Guy et al.
2024/0130981 A1 4/2024 Wilkhu
2024/0131041 A1 4/2024 Tse
2024/0165048 A1 5/2024 Guy
2024/0207220 A1 6/2024 Guy et al.
2024/0215910 A1 7/2024 Tse et al.
2024/0226032 A9 7/2024 Wilkhu et al.
2024/0226123 A9 7/2024 Tse
2024/0238218 A1 7/2024 Silcock et al.
2024/0254066 A1 8/2024 Silcock et al.
2024/0254072 A1 8/2024 Silcock et al.

FOREIGN PATENT DOCUMENTS

GB 2539472 A 12/2016
GB 2548873 A 10/2017
WO WO-0103690 A1 1/2001
WO WO-2015193667 A1 12/2015
WO WO-2015193668 A1 12/2015
WO WO-2016094810 A2 6/2016
WO WO-2016203239 A1 12/2016
WO WO 2017/168138 A1 10/2017
WO WO-2018061007 A1 4/2018
WO WO-2018205022 A1 11/2018
WO WO 2019/207319 A1 10/2019

OTHER PUBLICATIONS

U.S. Appl. No. 16/314,569, filed Dec. 31, 2018.
U.S. Appl. No. 16/314,583, filed Dec. 31, 2018.
U.S. Appl. No. 16/328,209, filed Feb. 25, 2018.

(56) References Cited

OTHER PUBLICATIONS

U.S. Appl. No. 16/467,639, filed Jun. 7, 2019.
U.S. Appl. No. 16/486,750, filed Aug. 16, 2019.
U.S. Appl. No. 16/591,702, filed Oct. 3, 2019.
U.S. Appl. No. 16/624,106, filed Dec. 18, 2019.
U.S. Appl. No. 16/651,751, filed Mar. 27, 2020.
U.S. Appl. No. 16/737,707, filed Jan. 8, 2020.
U.S. Appl. No. 16/764,701, filed May 15, 2020.
U.S. Appl. No. 16/768,241, filed May 29, 2020.
U.S. Appl. No. 16/791,940, filed Feb. 14, 2020.
U.S. Appl. No. 16/893,018, filed Jun. 4, 2020.
U.S. Appl. No. 16/935,005, filed Jul. 21, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/960,665, filed Jul. 8, 2020.
U.S. Appl. No. 16/989,605, filed Aug. 10, 2020.
U.S. Appl. No. 17/011,715, filed Sep. 3, 2020.
U.S. Appl. No. 17/025,130, filed Sep. 18, 2020.
U.S. Appl. No. 17/050,956, filed Oct. 27, 2020.
U.S. Appl. No. 17/068,326, filed Oct. 12, 2020.
U.S. Appl. No. 17/119,873, filed Dec. 11, 2020.
U.S. Appl. No. 17/147,005, filed Jan. 12, 2021.
U.S. Appl. No. 17/188,766, filed Mar. 1, 2021.
U.S. Appl. No. 17/198,965, filed Mar. 11, 2021.
U.S. Appl. No. 17/242,075, filed Apr. 27, 2021.
U.S. Appl. No. 17/296,076, filed May 21, 2021.
U.S. Appl. No. 14/340,885, filed Jun. 7, 2021.
U.S. Appl. No. 17/424,682, filed Jul. 21, 2021.
U.S. Appl. No. 17/426,442, filed Jul. 28, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.

Aniline, O. & Pitts, F. N., “Phencyclidine (PCP): A Review and Perspectives,” CRC Critical Reviews in Toxicology, 10(2):145-177 (1982); doi: 10.3109/10408448209041322.
Citti, C. et al., “Analysis of impurities of cannabidiol from hemp. Isolation, characterization and synthesis of cannabidibutol, the novel cannabidiol butyl analog,” Journal of Pharmaceutical and Biomedical Analysis, 175:112752 (2019); doi.org/10.1016/j.jpba.2019.06.049.
Cuesta, M. J. et al., “Effects of olanzapine and other antipsychotics on cognitive function in chronic schizophrenia: a longitudinal study,” Schizophrenia Research, 48:17-28 (2001).
Lewis, M. M. et al., “Chemical Profiling of Medical Cannabis Extracts,” ACS Omega, 2:6091-6103 (2017).
McGuire, P. et al., “Cannabidiol (CBD) as an Adjunctive Therapy in Schizophrenia: A Multicenter Randomized Controlled Trial,” Am J Psychiatry, 175:225-231 (2018); doi: 10.1176/appi.ajp.2017.17030325.
Rosenberg, E. C. et al., “Therapeutic effects of cannabinoids in animal models of seizures, epilepsy, epileptogenesis, and epilepsy-related neuroprotection,” Epilepsy Behav, 70(Pt B):319-327 (2017).
EPIDIOLEX® (cannabidiol) oral solution, CV, Prescribing Information, 2018, 30 pages; https://www.accessdata.fda.gov/drugsatfda_docs/label/2018/210365lbl.pdf.
Harvey, D. J., “Characterization of the Butyl Homologues of Delta1-tetrahydrocannabinol, Cannabinol and Cannabidiol in Samples of Cannabis by Combined Gas Chromatography and Mass Spectrometry,” J. Pharm. Pharmac., 28:280-285 (1976).
Hill, “Cannabidivarin-rich cannabis extracts are anticonvulsant in mouse and rat via a CB 1 receptor-independent mechanism,” British Journal of Pharmacology, 170(3):679-692 (2013).
Morales, P. et al., “An Overview on Medicinal Chemistry of Synthetic and Natural Derivatives of Cannabidiol,” Frontiers in Pharmacology, 8:422 (2017); doi:10.3389/fphar.2017.00422, 18 pages.
Pertwee, R. G., “The Pharmacology and Therapeutic Potential of Cannabidiol,” Cannabinoids, Chapter 3, DiMarzo, V. (Ed.), pp. 32-83 (2004).

Figure 1. Evaluation of Cannabidiol-C4 (CBD-C4) in the MES test in the mouse
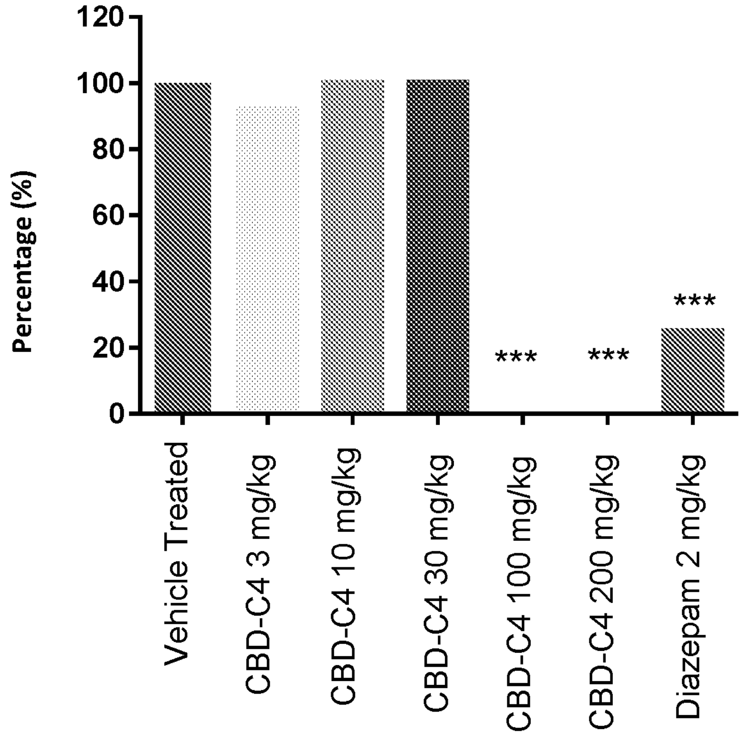

Figure 2. The effect of CBD-C4 and risperidone on sniffing duration in scPCP treated rats
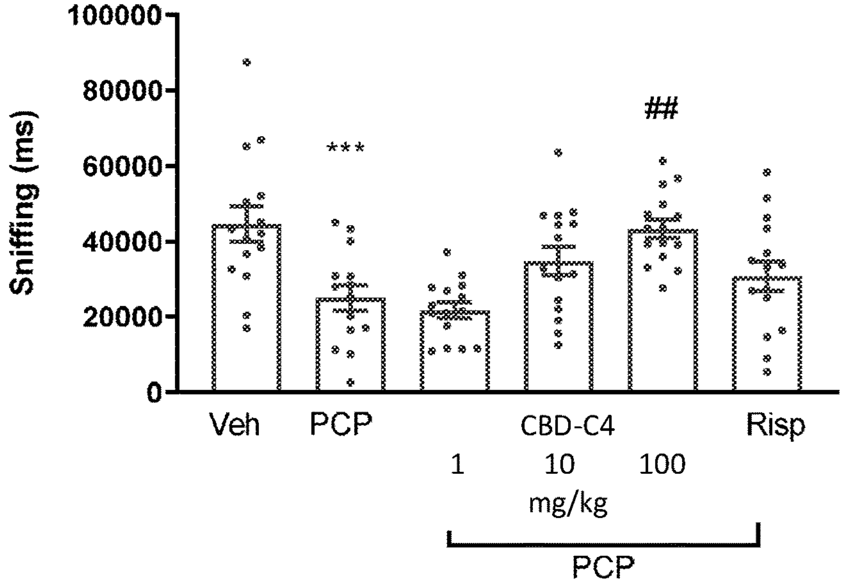
Data are shown as mean ± s.e.m. sniffing duration ms (n=14-15 per group). ***P<0.001; significant reduction in sniffing behaviour compared to vehicle. ##P<0.01; significant increase in sniffing duration compared to scPCP group. One-way ANOVA followed by planned comparisons with Sidak's correction.

Figure 3. The effect of CBD-C4 and risperidone on following duration in scPCP treated rats

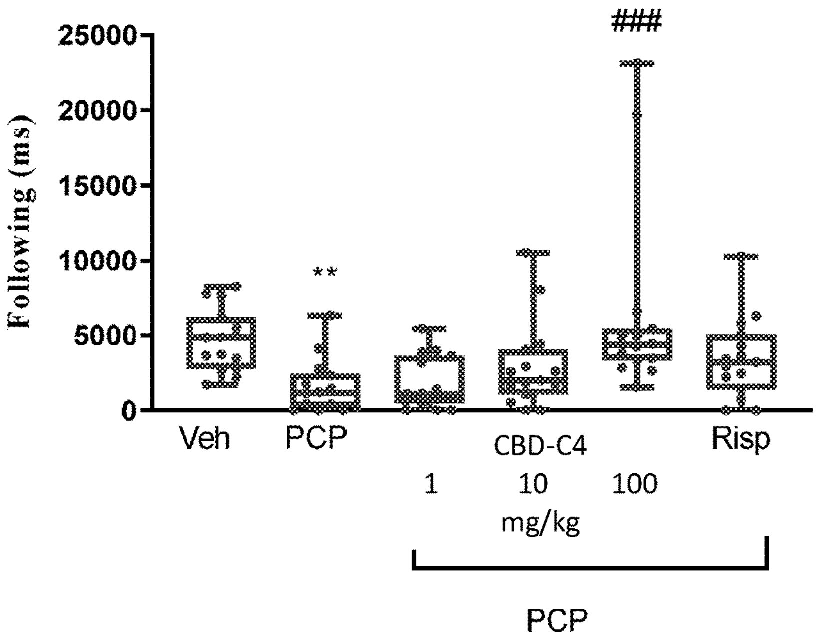

Data are shown as median and interquartile ranges of following duration ms (n=14-15 per group). **P<0.01; significant decrease in following duration compared to vehicle. ###P<0.001; significant increase in following duration compared to scPCP. Kruskal-Wallis followed by planned comparisons with Dunn's correction.

Figure 4. The effect of CBD-C4 and risperidone on avoidance duration in scPCP treated rats
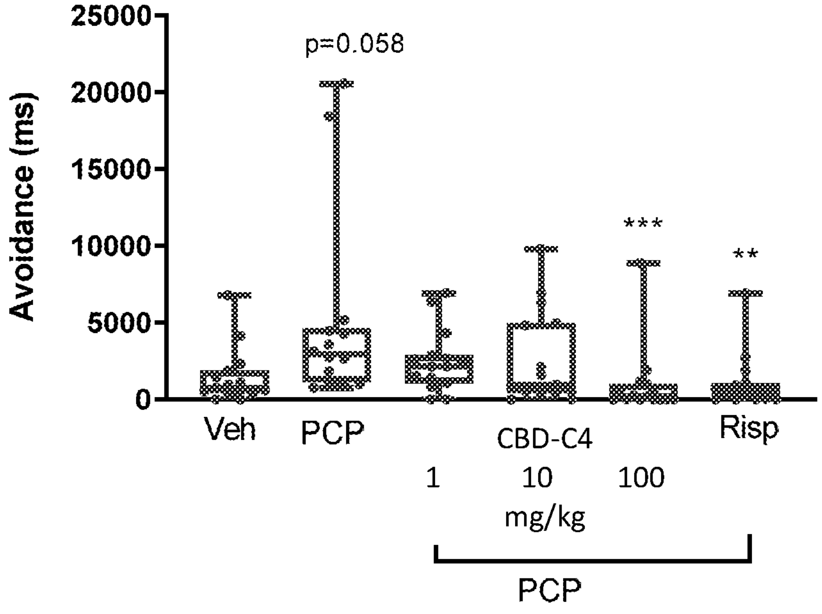
Data are shown as median and interquartile ranges of avoidance duration ms (n=14-15 per group). P<0.01, *P<0.001; significant decrease in avoidance behaviour compared to scPCP. Kruskal-Wallis followed by planned comparisons with Dunn's correction.

CANNABIDIOL-TYPE CANNABINOID COMPOUND

CROSS-REFERENCE TO RELATED APPLICATIONS

This application claims the benefit of International PCT Application No. PCT/GB2019/053284, filed Nov. 20, 2019; and Great Britain Application No. 1818935.7, filed Nov. 21, 2018; each of the aforementioned applications are incorporated herein by reference in its entirety.

FIELD OF THE INVENTION

The present invention relates to a cannabidiol (CBD) type cannabinoid compound for use as a medicament.

The CBD-type cannabinoid, cannabidiol-C4 (CBD-C4), is a naturally occurring cannabinoid that can be found in minor quantities in the *cannabis* plant. Furthermore, the cannabinoid can be produced by synthetic means.

Disclosed herein are data which demonstrate the efficacy of CBD-C4 in models of disease. In addition, a method for the production of CBD-C4 is described.

BACKGROUND TO THE INVENTION

Cannabinoids are natural and synthetic compounds structurally or pharmacologically related to the constituents of the *cannabis* plant or to the endogenous agonists (endocannabinoids) of the cannabinoid receptors CB1 or CB2. The only way in nature in which these compounds are produced is by the *cannabis* plant. *Cannabis* is a genus of flowering plants in the family Cannabaceae, comprising the species *Cannabis sativa, Cannabis indica*, and *Cannabis ruderalis* (sometimes considered as part of *Cannabis sativa*).

*Cannabis* plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPRS. The principle cannabinoids present in *cannabis* plants are cannabinoid acids Δ9-tetrahydrocannabinolic acid (Δ9-THCA) and cannabidiolic acid (CBDA) with small amounts of their respective neutral (decarboxylated) cannabinoids. In addition, *cannabis* may contain lower levels of other minor cannabinoids. "Chemical composition, pharmacological profiling, and complete physiological effects of these medicinal plants, and more importantly the extracts from *cannabis*, remain to be fully understood." Lewis, M. M. et al., ACS Omega, 2, 6091-6103 (2017).

Crude extracts from *cannabis* plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids. See for example US 2014/0298511.

The present invention encompasses the surprising discovery that a minor cannabinoid related to CBD has therapeutic efficacy. This compound, cannabidiol-C4 (CBD-C4) can be extracted from the *cannabis* plant and purified or may be produced synthetically.

As stated, cannabinoids are a class of compounds which may be derived naturally from the *cannabis* plant or produced synthetically via chemical synthesis.

More than 100 different cannabinoids produced by *cannabis* have been identified. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the *cannabis* plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of *cannabis*.

Synthetic cannabinoids are compounds that have a cannabinoid-like structure and are manufactured using chemical means rather than by the plant.

Certain cannabinoids are described in more detail below.

Cannabidiol (CBD) is a major cannabinoid constituent of *Cannabis* species, such as the hemp plant (*Cannabis sativa*). Unlike other cannabinoids, such as THC, cannabidiol does not bind CB1 or CB2, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

Tetrahydrocannabinol (THC) is the principal psychoactive constituent of *cannabis*. THC is a partial agonist at the CB1 and CB2 receptors. Synthetic THC or dronabinol is approved for the treatment of loss of appetite in AIDS patients and nausea and vomiting caused by cancer chemotherapy.

Of the over 100 natural cannabinoids identified in *Cannabis sativa*, seven have been classified as CBD-type compounds, these cannabinoids have the same absolute configuration as CBD. These are: CBD, Cannabidiolic acid (CBDA), Cannabidivarin (CBDV), Cannabidivarin acid (CBDVA), Cannabidiol-C1 (CBD-C1), Cannabidiol-C4 (CBD-C4) and Cannabidiol monomethyl ether (CBDM).

Cannabidiolic acid (CBDA) is the main form in which CBD exists in the *cannabis* plant. It is converted into CBD after decarboxylation.

Cannabidivarin (CBDV) is a homolog of CBD, with the side-chain shortened by two methylene bridges. CBDV is a non-psychoactive cannabinoid and has been shown to have anticonvulsant activity in a mouse model of epilepsy.

Cannabidiol-C1 (CBD-C1) also known as cannabidiorcol is a homolog of CBD, with the side-chain shortened by four methylene bridges. CBD-C1 occurs naturally in plants producing CBD but has not been shown to have any therapeutic effects.

Cannabidiol-C4 (CBD-C4) also known as nor-cannabidiol is a homolog of CBD, with the side-chain shortened by one methylene bridge. CBD-C4 occurs naturally in plants producing CBD and prior to the present invention has not been shown to have any therapeutic effects.

The present invention demonstrates data for the first time to indicate that the compound cannabidiol-C4 may have therapeutic benefit.

BRIEF SUMMARY OF THE DISCLOSURE

In accordance with a first aspect of the present invention there is provided cannabidiol-C4 (CBD-C4) for use as a medicament.

Preferably the CBD-C4 is in the form of a plant extract. More preferably the CBD-C4 is in the form of a highly purified extract of *cannabis*.

Preferably the highly purified extract comprises at least 80% (w/w) CBD-C4, more preferably the highly purified extract comprises at least 85% (w/w) CBD-C4, more preferably the highly purified extract comprises at least 90% (w/w), more preferably the highly purified extract comprises at least 95% (w/w) CBD-C4, more preferably still the highly purified extract comprises at least 98% (w/w) CBD-C4.

Alternatively, the CBD-C4 is present as a synthetic compound.

Preferably the dose of CBD-C4 is greater than 100 mg/kg/day. More preferably the dose of CBD-C4 is greater than 250 mg/kg/day. More preferably the dose of CBD-C4 is greater than 500 mg/kg/day. More preferably the dose of CBD-C4 is greater than 750 mg/kg/day. More preferably the dose of CBD-C4 is greater than 1000 mg/kg/day. More preferably the dose of CBD-C4 is greater than 1500 mg/kg/day.

Alternatively, the dose of CBD-C4 is less than 100 mg/kg/day. More preferably the dose of CBD-C4 is less than 50 mg/kg/day. More preferably the dose of CBD-C4 is less than 20 mg/kg/day. More preferably the dose of CBD-C4 is less than 10 mg/kg/day. More preferably the dose of CBD-C4 is less than 5 mg/kg/day. More preferably the dose of CBD-C4 is less than 1 mg/kg/day. More preferably the dose of CBD-C4 is less than 0.5 mg/kg/day.

In accordance with a second aspect of the present invention there is provided a composition for use as a medicament comprising cannabidiol-C4 (CBD-C4), and one or more pharmaceutically acceptable excipients.

In accordance with a third aspect of the present invention there is provided a cannabidiol-C4 (CBD-C4) for use in the treatment of epilepsy.

In accordance with a fourth aspect of the present invention there is provided a cannabidiol-C4 (CBD-C4) for use in the treatment of epilepsy.

In accordance with a fifth aspect of the present invention there is provided a method for the production of cannabidiol-C4.

BRIEF DESCRIPTION OF THE DRAWINGS

Embodiments of the invention are further described hereinafter with reference to the accompanying drawings, in which:

FIG. 1 shows the effect of CBD-C4 in the maximal electroshock (MES) test in mice;

FIG. 2 shows the effect of CBD-C4 and risperidone on sniffing duration in scPCP treated rats;

FIG. 3 shows the effect of CBD-C4 and risperidone on following duration in scPCP treated rats; and FIG. 4 shows the effect of CBD-C4 and risperidone on avoidance duration in scPCP treated rats.

CANNABINOIDS AND THEIR ABBREVIATIONS

The cannabinoids described in the present application are listed below along with their standard abbreviations.

CBD Cannabidiol

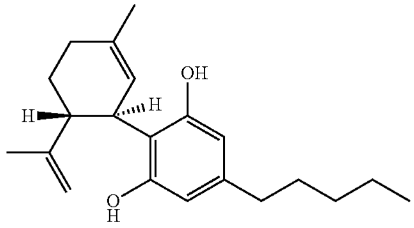 [SMILES: C=C(C)[C@@H]1CCC(C)=C[C@H]1c1c(O)cc(CCCCC)cc1O]

CBD-C4 Cannabidiol-C4

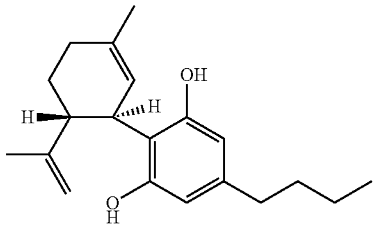 [SMILES: C=C(C)[C@@H]1CCC(C)=C[C@H]1c1c(O)cc(CCCC)cc1O]

DETAILED DESCRIPTION

Example 1: Evaluation of Cannabidiol-C4 (CBD-C4) for Anticonvulsant Activity Using the Maximal Electroshock (MES) Test in the Mouse The efficacy of CBD-C4 was tested in a mouse model of seizure, the maximal electroshock (MES) test.

Methods

Mice were administered MES (50 mA, rectangular current: 0.6 ms pulse width, 0.4 s duration, 50 Hz) via corneal electrodes connected to a constant current shock generator (Ugo Basile: type 7801). The number of tonic convulsions was recorded.

Twelve mice were studied per group. The test was performed blind.

The test substance, CBD-C4, was evaluated at 5 doses (3, 10, 30, 100 and 200 mg/kg), administered i.p. 60 minutes before MES, and compared with a vehicle control group (administered under the same experimental conditions).

Diazepam (2 mg/kg i.p.), administered i.p. 30 minutes before MES, was used as a reference substance and was compared with a vehicle group (administered i.p. 60 minutes before MES).

Data was analysed by comparing treated groups with the appropriate vehicle control using Fisher's Exact Probability tests.

Results

FIG. 1 demonstrates the data produced in this experiment.

In the vehicle group, all mice tested displayed tonic convulsions after electrical stimulation.

In the CBD-C4 treated mice, those treated at doses of 100 and 200 mg/kg, administered i.p. 60 minutes before the test, resulted in a significant decrease in the number of mice showing tonic convulsions, as compared with vehicle controls (−100%, $p<0.001$ at both doses). No effects were observed at lower doses (3, 10 and 30 mg/kg).

In the diazepam (2 mg/kg) treated group, administered i.p. 30 minutes before the test, these mice had a significant decrease in the number of tonic convulsions, as compared with vehicle controls (−75%, $p<0.001$).

Conclusions

These data demonstrate for the first time a therapeutic effect for the compound CBD-C4.

These data are significant as they provide heretofore unknown evidence that this cannabinoid which is found in minor quantities in extracts of *cannabis* plant may be of therapeutic value.

Example 2: Evaluation of Cannabidiol-C4 (CBD-C4) as a Therapeutic Agent

Example 1 demonstrated that CBD-C4 was efficacious in a mouse model of seizure Demonstration of therapeutic efficacy is only of value if the compound is found to have acceptable toxicology.

As such the compound CBD-C4 was tested in a range of toxicology screens to determine the no-observed-adverse-effect-level (NOAEL).

In order to test for genotoxicity, the Ames test and the COMET and Micronucleus assay were performed. No genotoxicity was observed in either test.

A 13-week oral toxicity study in rats was also undertaken. CBD-C4 was administered in a sesame oil formulation at doses of 1, 10 and 100 mg/kg. The NOAEL was considered to be 100 mg/kg CBD-C4.

An embryo-foetal development study in rats was also undertaken. CBD-C4 was administered in a sesame oil formulation at doses of 1, 10 and 100 mg/kg. The NOAEL was considered to be 100 mg/kg CBD-C4.

Further details of the methodology and results obtained are described below.

1. Ames Test

The aim of this study was to evaluate the potential mutagenic activity of CBD-C4 by examining its ability to revert five histidine-requiring strains of *Salmonella typhimurium* in the absence and presence of a rat liver metabolising system (S-9).

Methods

CBD-C4 was tested at final concentrations per plate of 5, 16, 50, 160, 500, 1600 and 5000 μg/plate.

Control treatments were performed with 2-nitrofluorene (2NF) at a final concentration of 5 μg/plate; Sodium azide ($NaN_3$) at a final concentration of 2 μg/plate; 9-aminoacridine (AAC) at a final concentration of 50 μg/plate; Mitomycin C (MMC) at a final concentration of 0.2 μg/plate; Benzo[a]pyrene (B[a]P) at a final concentration of 10 μg/plate; and 2-aminoanthracene (AAN) at a final concentration of 5 and 20 μg/plate.

Treatments were carried out both in the absence and presence of S-9 by addition of either buffer solution or 10% S-9 mix respectively.

Five strains of *Salmonella typhimurium* bacteria (TA98, TA100, TA1535, TA1537 and TA102) were used in this study.

Bacteria were cultured at 37±1° C. for 10 hours in nutrient broth, containing ampicillin or ampicillin and tetracycline as appropriate, to provide bacterial cultures in the range of approximately 108 to 109 cells/mL, based on cell count data from testing of each strain batch.

Incubation was carried out with shaking in an anhydric incubator, set to turn on using a timer switch. All treatments were completed within 6 hours of the end of the incubation period.

The inocula were taken from master plates or vials of frozen cultures, which had been checked for strain characteristics (histidine dependence, rfa character, uvrB character and resistance to ampicillin or ampicillin plus tetracycline).

CBD-C4 was tested for mutation (and toxicity) in the five strains of *Salmonella typhimurium* (TA98, TA100, TA1535, TA1537 and TA102), in a single experiment, at the concentrations detailed previously, using triplicate plates without and with S-9.

Vehicle controls were included in quintuplicate, and positive controls were included in triplicate without and with S-9.

These plating's were achieved by the following sequence of additions to molten agar at 46±1° C.: 0.1 mL bacterial culture >0.1 mL test article solution or control >0.5 mL 10% S-9 mix or buffer solution followed by rapid mixing and pouring on to Vogel-Bonner E agar plates. When set, the plates were inverted and incubated at 37±1° C. protected from light for 3 days.

Following incubation, these plates were examined for evidence of toxicity to the background lawn, and where possible revertant colonies were counted.

The background lawns of the plates were examined for signs of toxicity. Other evidence of toxicity may have included a marked reduction in revertants compared to the concurrent vehicle controls and/or a reduction in mutagenic response. Where mutation data from fewer than five treatment concentrations was obtained, an evaluation of the mutation data for the study as a whole was made.

Results

Following CBD-C4 treatments of all the test strains in the absence and presence of S-9, no increases in revertant numbers were observed which were 1.5-fold (in strain TA102), 2-fold (in strains TA98 and TA100) or 3-fold (in strains TA1535 and TA1537) the concurrent vehicle control.

This study was considered therefore to have provided no evidence of any CBD-C4 mutagenic activity in this assay system.

Conclusion

It is concluded that the compound CBD-C4 does not induce mutation in the five strains of *Salmonella typhimurium* tested.

2. Rat Micronucleus and Alkaline Comet Assay

CBD-C4 was tested for its potential to induce micronuclei (MN) in the polychromatic erythrocytes (PCE) of the bone marrow of treated rats to induce DNA damage in the liver of the same animals.

Methods

CBD-C4 was administered at a dose of 125, 250 and 500 mg/kg/day during this study. Vehicle and a positive control of ethyl methanesulfonate (EMS) at a dose of 150 mg/kg/day were tested alongside the CBD-C4.

A range finding study was performed on 9 male young adult out-bred Sprague Dawley rats justifying the chosen dose levels of CBD-C4 used during the study.

Animals were allocated into groups of six with the exception of the positive control which comprised three animals.

Rats were dosed by oral gavage with test article suspended in sesame oil, vehicle (sesame oil) or positive control.

Blood samples were taken for bioanalysis and tissue samples were removed from animals at necropsy from the liver and femur.

Bone marrow sampling, micronucleus slide preparation and comet cell suspensions were undertaken to determine level of toxicity of CBD-C4.

Results

CBD-C4 treated rats at all dose levels exhibited group mean percentage polychromatic erythrocytes (PCE) values that were similar to, or higher than the vehicle control group and which fell within the laboratory's historical control data, thus confirming there was no evidence of test article related bone marrow toxicity.

At all doses, CBD-C4 treated rats displayed micronucleus PCE frequencies that were comparable with the vehicle control group and which fell within the laboratory's historical control data. There were no statistically significant increases in micronucleus frequency for any of the groups receiving the test article compared to the concurrent vehicle control.

There was no dose-related increase in % hedgehogs in liver following treatment with CBD-C4, thus demonstrating that treatment with CBD-C4 did not cause excessive DNA damage (which can interfere with Comet analysis) following oral by gavage administration.

Group mean tail intensity and tail moment values for all groups of animals treated with CBD-C4 were comparable with the group mean vehicle control data. There were no statistically significant differences in tail intensity between treated and control groups. All individual animal data at all dose levels were generally consistent with the vehicle control animals and fell within the laboratory's historical control data.

Conclusion

It is concluded that CBD-C4, did not induce an increase in micronuclei in the polychromatic erythrocytes of the bone marrow in male rats treated up to 500 mg/kg/day (an estimate of the maximum tolerated dose for this study) under the experimental conditions employed.

In the same animals CBD-C4 did not induce DNA damage in the liver, as analysed by the Comet assay.

3. 13-Week Oral Toxicity Study in Rats

The objective of the study was to determine the toxicity of CBD-C4 following daily oral (gavage) administration to the rat for 4 and 13 weeks. The toxicokinetic profile of the CBD-C4 was also assessed.

Methods

Groups of 10 male and 10 female rats were doses at 1, 10 and 100 mg/kg/day for either 4 or 13 weeks.

Assessment of toxicity of CBD-C4 was based on mortality, clinical observations, post-dose observations, body weights, food consumption, ophthalmic observations, clinical and anatomic pathology.

Blood samples were collected on days 1 and 28 and week 13 of the study.

Results

CBD-C4 was well tolerated. There were no test article-related deaths, no adverse clinical signs and no adverse changes in clinical pathology parameters. Food consumption, body weight, body weight gains and ophthalmoscopy were unaffected by treatment with CBD-C4.

Large livers with correlating organ weight increase and centrilobular hypertrophy were observed at both the interim and main study terminal kills after 4 and 13-weeks of treatment, predominantly at 100 mg/kg/day.

Conclusion

In conclusion, the daily oral gavage administration of CBD-C4 to rats at dose levels of 0 (vehicle control), 1, 10 or 100 mg/kg/day was well tolerated with no adverse in-life findings.

The liver changes that were observed are considered typical of the adaptive changes seen in response to challenge by xenobiotics and were non-adverse.

Under the conditions of this study, the high dose of 100 mg/kg/day was therefore considered to be the NOAEL.

4. Embryo-Foetal Development Study in Rats

The objective of the study was to determine the effects of CBD-C4 on the embryonic and foetal development of the rat. The toxicokinetic profile of CBD-C4 was also assessed.

Methods

Three groups of 20 time-mated female Wistar (Han) rats were given CBD-C4 once daily by the oral (gavage) route from Day 6 to Day 17 of gestation at dose levels of 1, 10 or 100 mg/kg/day (at a constant dose volume of 5 mL/kg), to cover the period of organogenesis.

A similar group of rats was given the vehicle, sesame oil, following the same regimen to act as controls.

Blood samples were taken for toxicokinetic evaluation at pre-dose, 1, 2, 4, 6 and 24 hours after dosing on Days 6 and 17 of gestation. Clinical observations, body weight and food consumption were recorded. On Day 21 of gestation (GD 21) the females were euthanised, and the progress and outcome of pregnancy was evaluated.

Foetuses were evaluated for external, visceral and skeletal malformations and variations.

Results

On GD 6, plasma concentrations of CBD-C4 were at a maximum at 2 hours post dose at a dose level of 1 mg/kg/day and at 6 hours at the higher dose levels. After 12 daily doses, on GD 17 of gestation, maximum concentrations were reached at 4 hours post dose at all dose levels.

On both sampling occasions, elimination of CBD-C4 from plasma was complete within 24 hours after dosing at the lowest dose level. However, at both higher dose levels, quantifiable levels of CBD-C4 remained in plasma 24 hours after dosing. On both sampling occasions, increases in CBD-C4 exposure (Cmax and AUC(0–t)) were supra-proportional to the increase in dose.

At each dose level, CBD-C4 exposure increased following 12 daily doses compared to after a single dose. The extent of accumulation decreased as dose level increased, from approximately 5-fold at 1 mg/kg/day to ca 2-fold at 100 mg/kg/day.

There was no mortality during the study and there were no treatment-related clinical observations.

Post dosing observations were limited to occasional mouth rubbing on return to the cage after dosing seen in all CBD-C4 groups and in the controls. These observations were considered to be associated with the oily vehicle used in the formulations.

Dose-related mean body weight loss was recorded for females that received 10 or 100 mg/kg/day for one day after the start of dosing on Day 6 of gestation. Mean body weight for females administered 1 mg/kg/day was unaffected by CBD-C4 administration.

Lower mean food consumption was observed for animals administered 100 mg/kg/day CBD-C4 for two days after the start of dosing compared with controls.

Mean food consumption for females administered 1 or 10 mg/kg/day was unaffected by CBD-C4 administration.

There was no effect on pregnancy parameters based on the number of implantations, the extent of pre- or post-implantation losses or the number of live foetuses.

There was no effect on mean foetal weight or on the percentage of male foetuses.

There were no CBD-C4-related foetal malformations and there were no malformations in foetuses maternally dosed at 1 or 100 mg/kg/day. At 10 mg/kg/day, there were two foetuses with malformations from different organ systems that did not show any developmental pattern. There were no noteworthy foetal variations in any of the groups maternally dosed with CBD-C4.

Conclusion

In conclusion, daily administration of CBD-C4 to pregnant Wistar (Han) rats at dose levels up to 100 mg/kg/day was well tolerated.

Transient body weight loss at 10 and 100 mg/kg/day and transient reduced food consumption at 100 mg/kg/day did not adversely affect the maternal animals or the pregnancies of these animals. In addition, there were no treatment-related foetal malformations or variations.

The No Observable Adverse Effect Level (NOAEL) for maternal and embryo-foetal toxicity was considered to be 100 mg/kg/day.

Example 3: Synthetic Production Method for Cannabidiol-C4 (CBD-C4)

As previously described the compound CBD-C4 is produced as a minor cannabinoid in the *cannabis* plant. In a highly purified extract of cannabidiol the amount of CBD-C4 which remains in the extract is not more than 0.5% (w/w).

The CBD-C4 levels are very consistent within cannabidiol BDS and range from 0.16 to 0.26% w/w with a mean level of 0.20% w/w.

As such the synthetic pathway described below details a methodology that can be used in order to produce the cannabinoid CBD-C4 in larger quantities.

The compounds are numbered, and their full names provided in the box below the pathway.

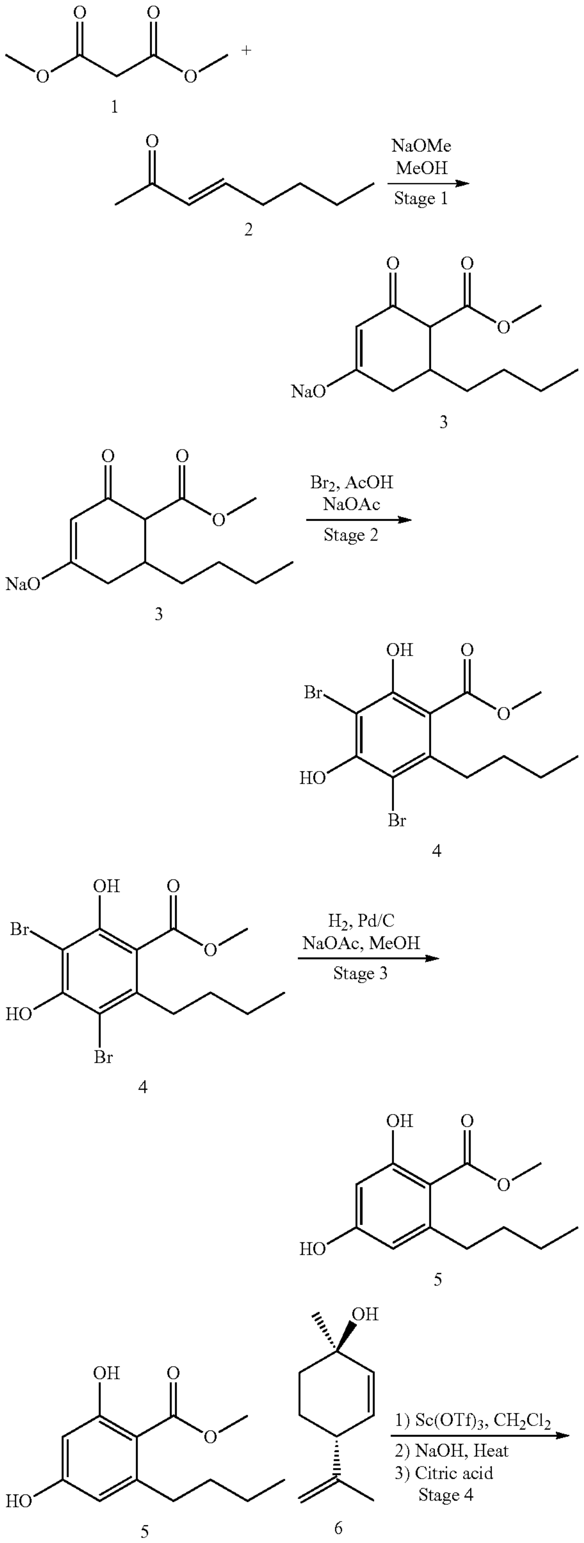

-continued

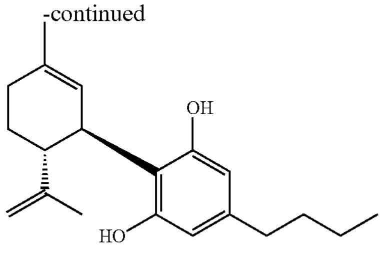

7

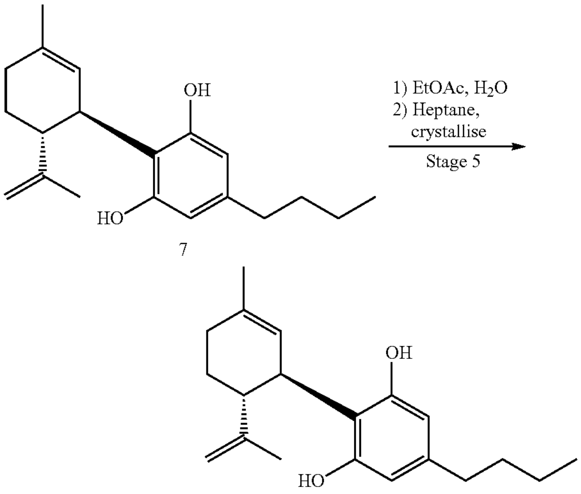

7

CBD-C4

| Compound | Name |
|---|---|
| 1 | dimethyl malonate |
| 2 | (E)-oct-3-en-2-one |
| 3 | sodium 5-butyl-4-(methoxycarbonyl)-3-oxocyclohex-1-en-1-olate |
| 4 | methyl 3,5-dibromo-2-butyl-4,6-dihydroxybenzoate |
| 5 | methyl 2-butyl-4,6-dihydroxybenzoate |
| 6 | (1R,4R)-1-methyl-4-(prop-1-en-2-yl)cyclohex-2-en-1-ol |
| 7 | (1'R,2'R)-4-butyl-5'-methyl-2'-(prop-1-en-2-yl)-1',2',3',4'-tetrahydro-[1,1'-biphenyl]-2,6-diol CBD-C4 |

Example 4: Evaluation of Cannabidiol-C4 (CBD-C4) in an Animal Model of Schizophrenia Phencyclidine (PCP), the psychotomimetic agent and non-competitive NMDA receptor antagonist is increasingly used to mimic characteristics of the schizophrenic symptom cluster in animals, in an effort to develop relevant models of the disease and identify novel therapeutic agents. The PCP based models of the disease have the advantage of reproducing not only the positive but also aspects of cognitive and negative symptoms of schizophrenia, some of which are correlated with clinical observations (Aniline and Pitts, 1982; Cuesta et al., 2001).

The present example describes the effects of CBD-C4 in an animal model for assessing the avolition domain of negative symptoms of schizophrenia, lack of social behaviour, using the sub-chronic administration of PCP.

PCP induces a social behaviour deficit in female rats in their interaction with a vehicle treated weight matched control rat. This deficit is not attenuated by the classical antipsychotic agent, haloperidol or by the anxiolytic agent chlordiazepoxide or the antidepressant, fluoxetine, but is attenuated by the novel antipsychotics, ziprasidone and aripiprazole.

The aim of the current study was to investigate the ability of CBD-C4 (3, 10 & 30 mg/kg IP; 60 min pre-treatment (ptt)) in comparison with risperidone (an atypical antipsychotic; 0.1 mg/kg IP; 60 min pre-treatment), to antagonise a sub-chronic PCP (scPCP; 2 mg/kg IP; twice daily for 7-days; 7 day wash out)-induced deficit in social behaviour in female Lister-Hooded rats.

Methods

Test Compounds

CBD-C4, PCP (Sigma) and risperidone (Sigma) were used in this study.

Animals and Housing Conditions

Animals Used:

180 female Lister Hooded rats were used for this experiment, of which 90 were used for the drug study and 90 weight-matched untreated conspecifics were used as the companion rat, and their behaviour was not scored.

Acclimatisation and Housing Conditions:

Rats were housed in groups of 5 under standard laboratory conditions under a 12-hr light: dark cycle, lights on at 0700 hr. Testing was carried out in the light phase. These studies were carried out in accordance with the Animals Scientific Procedures Act (UK, 1986).

Treatment and Dosing

Selection of Dose Levels:

CBD-C4 was used at doses of (3, 10, 30 mg/kg, i.p.) and risperidone was used at a dose of 0.1 mg/kg, i.p.

Route and Means of Administration:

Rats were randomly assigned to two treatment groups and treated with vehicle, n=15 (distilled water, i.p.) or PCP, n=75 (2 mg/kg, i.p. twice daily for 7-days). This was followed by a 7-day wash out period before the rats were tested following acute treatment with CBD-C4, risperidone or vehicle.

Risperidone (0.1 mg/kg) was dissolved in a minimum volume of acetic acid, made up to volume with distilled water and pH adjusted to 6 with 0.1M NaOH and administered via the i.p. route in a volume of 1 ml/kg, 60 min prior to testing.

CBD-C4 (3, 10 & 30 mg/kg) was dissolved in 2:1:17 (Ethanol:Cremophor EL:Saline 0.9%). CBD-C4 was administered via the i.p. route in a volume of 5 ml/kg, 60 min prior to testing.

Experimental Procedure

The social interaction test was performed in an open-field comprising a square box made of Plexiglas (52×52×31 cm) placed 27 cm above the floor on a moveable trolley. The floor of the box was white with black gridlines forming 9 identical squares on it. All other walls were black. A video camera connected to a video recorder and monitor was positioned above the box. The object used for the test consists of a heavy structure made of metal that cannot be displaced by the animals. Care was taken to ensure that these objects do not have natural significance for the rats.

After a 7 day drug-free period, the rats were habituated to the test environment and arena prior to the test day. Habituation consisted of placing all rats from one cage together in the empty test arena for one hour for three days including the day before the test day.

Pairs of rats, weight matched (15-20 g) and unfamiliar to each other, receiving either no treatment (n=90 "conspecific" rats) or different treatments (PCP; n=15 "tested" rats, Vehicle; n=15 "tested" rats, or PCP+drug; n=60 "tested"

rats) were placed in the test arena together for 10 minutes and behavior assessed as described below.

An inanimate object such as an unopened drink can was also placed in the centre of the arena to measure any differences in interaction of the test animal with an unfamiliar animal as opposed to an unfamiliar object. After each 10-minute trial, the object and arena were cleaned with 10% alcohol in an attempt to remove traces of any olfactory cues. All testing was carried out under standard room illumination levels (70 cd/$m^2$).

Behaviour in both trials was recorded on video for subsequent blind scoring. A behavioural scoring software program (Hindsight, Scientific programming services) was used to score the following parameters:

Investigative sniffing behaviour: sniffing the conspecific's snout or parts of the body including the anogenital region.

Following: rat moves after the conspecific i.e. a vehicle treated rat of the same species, around the arena.

Avoidances: actively turning away when approached by the conspecific animal.

Investigation of object: exploration of object placed in centre of the arena.

Locomotor activity is recorded by counting the total number of sectors (i.e. lines) crossed by the test rat.

Collection and Analysis of Brain and Blood Samples

Brain and blood samples were collected from all animals (n=90) immediately after completion of the social interaction test, which was 70 min post dosing. Brains were collected into labelled polypropylene tubes. Whole blood was taken into lithium heparin tubes and mixed, then centrifuged at 4° C. for 10 minutes at 5000 RPM. The resulting plasma was transferred into labelled polypropylene tubes, which were stored at −80° C. until analysis (data from this will be reported in a separate document).

Statistical Analysis

All data were assessed for normality using D'Agostino and Pearson normality test. Data that were non-normally distributed were analysed using Kruskal-Wallis followed by planned comparisons with Dunn's correction. Normally distributed data were analysed using one-way ANOVA followed by planned comparisons with Sidak's correction. All analyses were carried out by GW Research Ltd using GraphPad Prism V8.02.

Results

CBD-C4 at a dose of 30 mg/kg improved all the behavioural deficits induced by scPCP (sub-chronic PCP) in the social interaction test in female Lister Hooded rats as described below.

Sniffing

Mice that were treated with PCP demonstrated a significantly reduced sniffing behaviour ($P<0.001$). There was a significant increase in sniffing behaviour in the scPCP-treated rats that received CBD-C4 30 mg/kg ($P<0.01$) compared to scPCP as shown in FIG. 2.

Following

Mice that were treated with PCP demonstrated a significantly reduced following behaviour ($P<0.01$). CBD-C4 (30 mg/kg) significantly increased following behaviour compared to scPCP ($P<0.001$) as shown in FIG. 3.

Avoiding

The increase in the duration of avoidance activity in the scPCP-treated group just failed to reach statistical significance ($P=0.058$). CBD-C4 (30 mg/kg) and risperidone (0.1 mg/kg) significantly decreased avoidance behaviour when compared to the scPCP-treated group as shown in FIG. 4.

Object Exploration and Locomotor Activity

CBD-C4 and risperidone had no significant effect on object exploration or line crossings (data not shown).

DISCUSSION AND CONCLUSION

These results show that CBD-C4 at a dose of 30 mg/kg significantly reversed the sub-chronic PCP-induced deficits in sniffing and following behaviour. A numerical difference (increase) in avoidance behaviour between vehicle and scPCP treated animals was noted but was not statistically significant.

CBD-C4 at 30 mg/kg and risperidone significantly reduced avoidance behaviour when compared to the scPCP-treated group. The lower doses of CBD-C4 tested (3 and 10 mg/kg) had no effect on any of the parameters measured. Risperidone had no significant effect upon sniffing or following behaviour.

The results presented here suggest that CBD-C4 may have therapeutic value in the improvement of this aspect of the avolition domain of negative symptoms in schizophrenia.

The invention claimed is:

1. A method of treating a human or animal suffering from epilepsy comprising administering 20 mg/kg/day to 100 mg/kg/day of isolated or synthetic Cannabidiol C4 (CBD-C4) to the human or animal in need thereof to effectively treat the epilepsy in the human or animal wherein the isolated or synthetic Cannabidiol C4 (CBD-C4) is the only active ingredient administered in the method.

2. The method of claim 1, wherein the isolated or synthetic CBD-C4 is administered in a pharmaceutical composition.

3. The method of claim 1, wherein the isolated CBD-C4 comprises at least 80% (w/w) CBD-C4.

4. The method of claim 1, wherein the isolated CBD-C4 comprises at least 95% (w/w) CBD-C4.

5. The method of claim 2, wherein the pharmaceutical composition comprises sesame oil.

6. The method of claim 1, comprising administering 50 to 100 mg/kg/day of isolated or synthetic CBD-C4.

7. The method of claim 1, comprising administering 30 to 100 mg/kg/day of isolated or synthetic CBD-C4.

* * * * *